United States Patent
Nguyen et al.

[11] Patent Number: 5,772,609
[45] Date of Patent: Jun. 30, 1998

[54] GUIDEWIRE WITH VARIABLE FLEXIBILITY DUE TO POLYMERIC COATINGS

[75] Inventors: Kim Nguyen, San Jose; Chi J. Chung, Sunnyvale; Thomas J. Palermo, San Jose, all of Calif.

[73] Assignee: Target Therapeutics, Inc., Fremont, Calif.

[21] Appl. No.: 672,637

[22] Filed: Jun. 28, 1996

Related U.S. Application Data

[63] Continuation-in-part of Ser. No. 346,143, Nov. 29, 1994, abandoned, which is a continuation-in-part of Ser. No. 62,456, May 11, 1993, Pat. No. 5,409,015.

[51] Int. Cl.⁶ ........................................................ A61B 5/00
[52] U.S. Cl. ............................................................ 600/585
[58] Field of Search .................................... 128/657, 658, 128/772; 604/280–282

[56] References Cited

U.S. PATENT DOCUMENTS

| | | | |
|---|---|---|---|
| Re. 33,911 | 5/1992 | Samson et al. | 128/772 |
| 2,221,138 | 11/1940 | Hendrickson . | |
| 2,279,297 | 11/1942 | Bry . | |
| 2,905,178 | 9/1959 | Hilzinger, III . | |
| 3,174,851 | 3/1965 | Buehler et al. . | |
| 3,338,046 | 8/1967 | Baur et al. . | |
| 3,351,463 | 11/1967 | Rozner et al. . | |
| 3,416,531 | 12/1968 | Edwards . | |
| 3,453,742 | 7/1969 | Diederen . | |
| 3,528,406 | 9/1970 | Jeckel et al. . | |
| 3,547,103 | 12/1970 | Cook . | |
| 3,552,384 | 1/1971 | Pierie et al. . | |
| 3,753,700 | 8/1973 | Harrison et al. . | |
| 3,757,768 | 9/1973 | Kline . | |
| 3,789,841 | 2/1974 | Antoshkiw . | |
| 3,890,977 | 6/1975 | Wilson . | |
| 3,941,119 | 3/1976 | Corrales . | |
| 3,973,556 | 8/1976 | Fleischhacker et al. . | |
| 4,003,369 | 1/1977 | Heilman et al. . | |
| 4,020,829 | 5/1977 | Willson et al. . | |
| 4,178,810 | 12/1979 | Takahashi . | |
| 4,215,703 | 8/1980 | Willson . | |
| 4,430,083 | 2/1984 | Ganz et al. . | |
| 4,538,622 | 9/1985 | Samson et al. | 128/772 |
| 4,544,929 | 10/1985 | Lemelson | 346/9 |
| 4,545,390 | 10/1985 | Leary | 128/772 |
| 4,619,274 | 10/1986 | Morrison | 128/772 |
| 4,665,906 | 5/1987 | Jervis | 128/92 YN |
| 4,721,117 | 1/1988 | Mar et al. | 128/772 |

(List continued on next page.)

FOREIGN PATENT DOCUMENTS

| | | |
|---|---|---|
| 0014424 | 12/1982 | European Pat. Off. . |
| 0382974 | 8/1990 | European Pat. Off. . |
| 0491349 | 6/1992 | European Pat. Off. . |
| 0515201 | 11/1992 | European Pat. Off. . |
| 0519604 | 12/1992 | European Pat. Off. . |
| 4-9162 | 1/1992 | Japan . |
| WO 91/15152 | 10/1991 | WIPO . |
| WO 92/14506 | 9/1992 | WIPO . |

OTHER PUBLICATIONS

Kikuchi et al., "A new guidewire with kink-resistant core and low friction coating" *Cardiovasc. Intervent. Radiol.* (1989) 12:107–109.

*Primary Examiner*—Max Hindenburg
*Attorney, Agent, or Firm*—Morrison & Foerster, LLP

[57] ABSTRACT

This invention is a guidewire for guiding a catheter and is used for accessing a targeted site within a lumen system in a body. The guidewire or guidewire section has a wire core, a distal tip region, a polymeric tie layer, and a lubricious coating. The tie layer is preferably constructed to provide for sections of varying flexibility along the length of the guidewire. Variations of the tie layer provide for axially spaced sections of varying flexibility, radially layers of varying flexibility of both. In a special variation, the tie layer is constructed with at least one section providing increased stiffness distally.

23 Claims, 7 Drawing Sheets

U.S. PATENT DOCUMENTS

| | | | |
|---|---|---|---|
| 4,739,768 | 4/1988 | Engelson | 128/658 |
| 4,770,188 | 9/1988 | Chikama | 128/772 |
| 4,790,624 | 12/1988 | Van Hoye et al. | 350/96.26 |
| 4,846,186 | 7/1989 | Box et al. | 128/657 |
| 4,925,445 | 5/1990 | Sakamoto et al. | 604/95 |
| 4,934,380 | 6/1990 | de Toledo | 128/772 |
| 4,966,163 | 10/1990 | Kraus et al. | 128/772 |
| 4,969,890 | 11/1990 | Sugita et al. | 606/192 |
| 4,971,490 | 11/1990 | Hawkins | 128/772 |
| 4,984,581 | 1/1991 | Stice | 128/772 |
| 4,991,602 | 2/1991 | Amplatz et al. | 128/772 |
| 4,998,923 | 3/1991 | Samson et al. | 606/194 |
| 5,019,040 | 5/1991 | Itaoka et al. | 604/95 |
| 5,042,985 | 8/1991 | Elliott et al. | 606/192 |
| 5,050,606 | 9/1991 | Tremulis | 128/637 |
| 5,069,226 | 12/1991 | Yamauchi et al. | 128/772 |
| 5,095,915 | 3/1992 | Engelson | 128/772 |
| 5,111,829 | 5/1992 | de Toledo | 128/772 |
| 5,120,308 | 6/1992 | Hess | 604/95 |
| 5,129,890 | 7/1992 | Bates et al. | 604/281 |
| 5,143,085 | 9/1992 | Wilson | 128/772 |
| 5,144,959 | 9/1992 | Gambale et al. | 128/772 |
| 5,171,383 | 12/1992 | Sagaye et al. | 148/564 |
| 5,213,111 | 5/1993 | Cook et al. | 128/772 |
| 5,230,348 | 7/1993 | Ishibe et al. | 128/772 |
| 5,238,004 | 8/1993 | Sahatjian et al. | 128/772 |
| 5,267,574 | 12/1993 | Viera et al. | 128/772 |
| 5,333,620 | 8/1994 | Montafis et al. | 128/772 |
| 5,341,818 | 8/1994 | Abrams et al. | 128/772 |
| 5,406,960 | 4/1995 | Corso, Jr. | 128/772 |
| 5,409,015 | 4/1995 | Palermo | 128/772 |
| 5,443,907 | 8/1995 | Slaikeu et al. | 428/375 |
| 5,498,250 | 3/1996 | Prather | 604/280 |

GUIDEWIRE WITH VARIABLE FLEXIBILITY DUE TO POLYMERIC COATINGS

RELATED APPLICATIONS

This is a continuation-in-part of U.S. Ser. No. 08/346,143, filed Nov. 29, 1994, now abandoned, which in turn is a continuation-in-part of U.S. Ser. No. 08/062,456, filed May 11, 1993, now U.S. Pat. No. 5,409,015, issued Apr. 25, 1995.

FIELD OF THE INVENTION

This invention is in the general field of surgical devices and relates to guidewires that are used in surgical procedures to facilitate the placement of catheters within the vasculature of patients. Specifically, the present invention relates to a catheter guidewire for accessing a tissue target site via a small-lumen tortuous path within a target tissue. The guidewire device includes a core wire having various regions along its length coated with polymeric materials designed to provide differing flexural and torsional stiffness.

BACKGROUND OF THE INVENTION

Catheters are used increasingly as a means for delivering diagnostic and therapeutic agents to internal sites within the human body that can accessed through the body's circulatory lumen system, particularly through the vasculature. Because catheters often do not have sufficient column strength or torsional strength to be advanced and steered through such tortuous paths, a catheter guidewire is often used to guide the catheter.

One method of directing a catheter through the tortuous paths of these systems of lumen involves the use of a torqueable guidewire which is directed as a unit from a body access point such as the femoral artery to the tissue region where the target site is located. Typically the guidewire and the catheter are advanced by alternately moving the guidewire along a distance in the vessel pathway, holding the guidewire in place, and then advancing the catheter along the axis of the guidewire until it reaches the portion of the guidewire already advanced farther into the human body.

Performance of such guidewires are determined by well known functional characteristics. One such characteristic is its ability to be steered. The distal portion of the guidewire is manipulated or steered through the bends, loops and branches of a patient's vasculature by pulling, pushing and rotating the proximal end, which remains outside of the patient's body. Typically, the distal tip is slightly bent or shaped to facilitate the selection and advancement into one vascular branch over another. To accommodate this type of steering and selection, torque transmission should be controlled, such that a selected wire rotation at the proximal end produces a corresponding rotation at the distal end. To accommodate the advancement of the guidewire within the body lumen, and also the catheter over the guidewire, it is advantageous have a guidewire with low frictional properties.

In addition to steerability, a guidewire should be resistant to kinking. Kinking refers to a condition where the guidewire has been plastically deformed and is often characterized by a permanent localized deformation where the wire was kinked. A related condition, known as prolapse, occurs when the distal end of the guidewire bends back upon itself instead of advancing in the desired direction. Often when this happens, the elastic limit of the guidewire is exceeded and permanent deformation, or kinking, results.

Once the guidewire has been kinked, the performance of the device is substantially degraded. Higher friction will be encountered at the location of the kink, adversely effecting the torque transmission of the wire, as well as making it more difficult both to advance the wire within the vasculature and to advance the catheter over the wire.

One of the more perplexing characteristics effecting guidewire performance is the flexibility and stiffness of the various sections of the guidewire. For example, a guidewire having sufficient flexibility to access a difficult target site through tortuous vasculature will often lack the torsional stiffness to enable branch selection, the longitudinal stiffness to enable proper advancement without kinking or prolapse, and the flexural stiffness to allow the catheter to properly track over the guidewire. Further, because these properties are conflicting, guidewire constructions that tend to favor either flexibility or stiffness, do so at the expense of the other.

Often one desires to advance the catheter to a target site which is deep within a soft tissue, such as the brain or liver. Such sites can be reached only by a tortuous route through small vessels or ducts in the tissue, typically less than 3 mm in diameter. The difficulty in accessing such regions is that the guidewire must be sufficiently flexible to adapt itself to a tortuous path without damaging the walls of the vessels or ducts, and at the same time, stiff enough to allow the distal end of the guidewire to be rotationally and axially manipulated by way of the proximal end which is at a remote, external access site.

Catheter guidewires of this type are typically formed of a flexible, torqueable wire filament material, such as stainless steel or super-elastic alloy. The catheter guidewires used in guiding a catheter through the human vasculature have a number of variable flexibility constructions. For instance, U.S. Pat. Nos. 3,789,841; 4,545,390; and 4,619,274 show guidewires in which the distal end section of the wire is tapered along its length to allow greater flexibility in the remote distal section of the guidewire. This is generally desirable in many applications because the guidewire encounters the sharpest turns at the distal region.

Although a reduction in the diameter of the guidewire tends to increase flexibility, it also decreases stiffness resulting in a reduction of the ability to manipulate and steer the guidewire. The tapered section of the wire is often enclosed in a wire coil, typically a platinum coil, to increase the column strength of the tapered wire section without significant loss of flexibility in that region and also to increase the radial capacity of the guidewire to allow fine manipulation of the guidewire through the vasculature.

Others have suggested the use of guidewires made of various super-elastic alloys in an attempt to achieve some of the noted functional desires. These materials exhibit exceptional flexibility but are difficult to shape at the distal tip. Again, the high flexibility is often at the expense of the manipulative steering control.

Other guidewire constructions have employed a metal core wire with a plastic casing. One such guidewire design is found in U.S. Pat. No. 5,095,915 which shows a guidewire having at least two sections. The distal portion is encased in an elongated polymer sleeve having axially spaced grooves to allow increased bending flexibility of the sleeve.

Another such guidewire construction is found in U.S. Pat. No. 5,333,620. That guidewire includes a metal core wire, at least a portion of which is surrounded by a high performance plastic layer having a flexural modulus preferably of at least 150,000 p.s.i. A compliant jacket surrounds the high performance plastic layer as well as the distal portion of the metal core wire which was not covered by the high performance plastic. The compliant jacket contains or is covered with a lubricious material. Such lubricious coatings are used to decrease the friction of the guidewire. The compliant jacket is selected for the ability to bond both to the high performance plastic and to the lubricious coating. This is commonly referred to as a tie layer because it ties the lubricious coating to the substrate of the guidewire.

Other guidewires using different plastic coatings over the core wire do so specifically for the frictional properties attained. U.S. Pat. No. 5,443,907 involves a core wire having a distal section coated with a suitable tie layer for bonding a low friction hydrophilic coating and a proximal section coated with a material of greater friction to accommodate improved handling for the physician as the guidewire is manipulated.

It would be desirable to provide a guidewire construction which allows for sections of the guidewire to have different flexibility and stiffness according to the requirements of the medical procedure and the preference of the physician. None of these disclosures suggest the guidewire construction described below.

SUMMARY OF THE INVENTION

This invention is a guidewire, preferably a guidewire suitable for introduction into soft tissue target sites through small and tortuous vasculature within the human body. The guidewire has a wire core, at least a portion of which is covered with a polymeric tie layer. Covering at least a portion of the tie layer is a lubricious coating. The core wire is preferably constructed of a stainless steel or super-elastic alloy material. The tie layer is constructed to provide sections of greater or lesser flexibility along the length of the guidewire.

In one embodiment, the tie layer may be constructed to have axially spaced sections of different flexibility. The different sections may be made from a different material or from a common material with different hardness. A highly desirable variation of the inventive guidewire having a sectioned tie layer provides for at least one section to be less flexible that a axially adjacent proximal section.

In a preferred embodiment, the tie layer has a proximal section, a middle section, and a distal section. The proximal section is constructed to have the highest hardness (lowest flexibility), the middle section to have the lowest hardness, and the distal section to have a hardness greater than that of the middle section.

In another embodiment the tie layer is constructed to additionally have a radially adjacent inner or outer tie layer. In yet another embodiment the tie layer has at least one section of varying thickness. In a final embodiment, the tie layer has at least one section of varying thickness and a second section, the sections at least partially overlapping.

DESCRIPTION OF THE INVENTION

Figure 1:
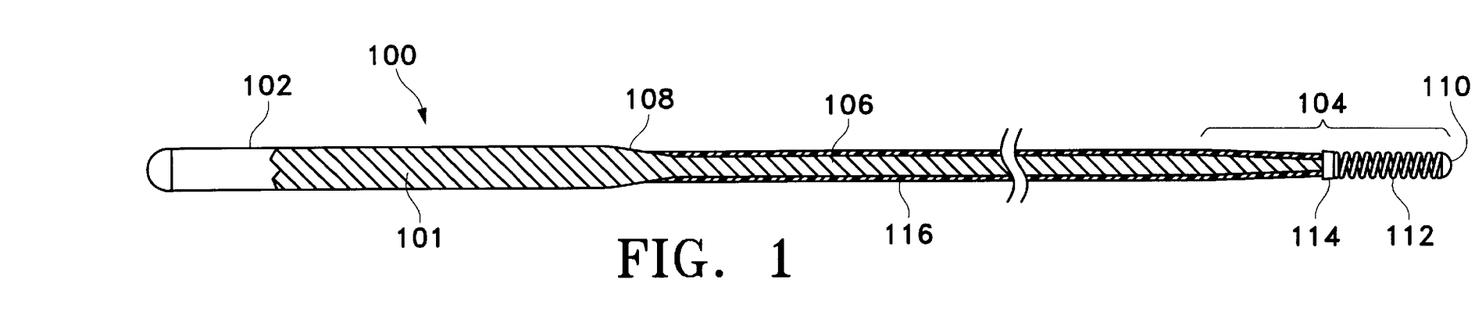
FIG. 1 shows a schematic side view (not to scale) of the major components of the inventive guidewire.

FIG. 1 shows an enlarged side view of guidewire (100) made according to the present invention. The guidewire (100) is adapted to access soft tissue target sites through small, tortuous vasculature and generally includes a proximal section (102), a middle section (106), and a distal section (112). Guidewire (100) has a total length typically between about 50 and 300 centimeters and is made up of wire core (101), which typically extends through a substantial portion of the length of the entire guidewire (100) and a polymeric tie layer (116) which has a lubricious coating over at least a portion of its surface. Each of the guidewire sections and the wire core construction according to the present invention is discussed in detail immediately below with regards to FIGS. 1 through 6. Further, inventive aspects of the tie layer are also described in detail below specifically with regards to FIGS. 7 through 13.

Wire core (101) is formed of a flexible torqueable wire filament material, typically stainless steel or a super-elastic alloy (e.g. a nickel/titanium alloy), but could be any other common construction such as a composite construction of at least two different materials or including a hypotube section. The wire core (101) may be made from combinations of materials along its length or from radial layers of different materials to yield the desired functional properties. Preferably, wire core (101) is made from a stainless steel or super-elastic alloy wire. More preferably the wire core (101) is made from shape memory alloys which exhibit super-elastic/pseudo-elastic shape recovery characteristics (see, for instance, U.S. Pat. Nos. 3,174,851, 3,351,463 and 3,753,700. One such well-known alloy is nitinol, a nickel-titanium alloy. Most preferably, wire core (101) is constructed of nitinol material which is nominally 50.6%±0.2% Ni and the remainder Ti. The alloy should contain no more than about 500 parts per million of any of O, C, or N. Typically such commercially available materials will be sequentially mixed, cast, formed, and separately co-worked to 30–40%, annealed and stretched. Most preferably the wire core (101) is made from Nitonol.

The proximal section (102) of guidewire (100) preferably has a uniform diameter (along its elongated length) of about 0.010 to 0.025 inches, preferably 0.010 to 0.018 inches and may be coated or uncoated by additional polymeric layers as discussed below. The relatively more flexible distal section (104) extends for 3 to 30 centimeters or more of the distal end of the guidewire (100). There may be a middle section (106) having a diameter intermediate between the diameter of the two portions of the wire adjoining the middle section. The middle section (106) may be continuously tapered, may have a number of tapered sections or sections of differing diameters, or may be of a uniform diameter along its length.

In forming the stepped or tapered sections of guidewire (100) of the present invention, step grinding can be used to form relatively short tapered segments. Methods of forming relatively long, continuous tapered cores and nonlinear tapered regions are well known.

If middle section (106) is of a generally uniform diameter, the guidewire core may neck down as is seen at (108). The distal section (104) of the guidewire (100) typically has an end cap (110), a fine wire coil (112), and a solderjoint (114). The fine wire coil (112) may be radiopaque and made from materials including but not limited to platinum and its alloys. Specific preferred variations of the distal section (104) are described below. The end cap (110) may be radiopaque to allow knowledge of the position of the coil (112) during the process of inserting the catheter and traversal of the guidewire through the vasculature. All or part of the guidewire proximal section (102) and middle section (106) and distal section (104) may be coated with inventive tie layer (116) of polymeric material. As described in detail below, the tie layer (116) may comprise multiple sections or multiple layers of various configurations to advantageously provide for sections of improved flexibility and torqueability. Highly desirable embodiments of the inventive tie layers provide for increased stiffness distally. This invention further includes portions or sections of the guidewire described above further having a slippery coating thereon, e.g., a hydrophilic polymeric coating.

Figure 2:
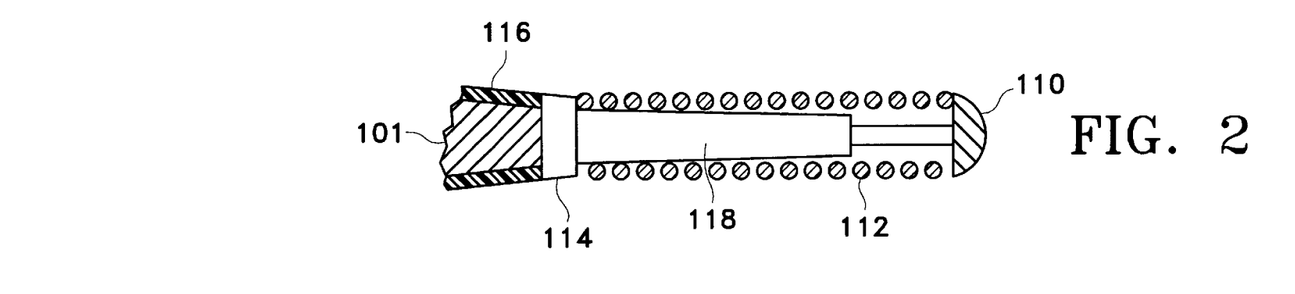
FIG. 2 is a partial cutaway side view of one embodiment of the distal tip of the FIG. 1 device.

FIG. 2 shows a partial cutaway of one embodiment of the distal section (104) of FIG. 1. The wire core (101) is shown at least partially coated with polymer (116) and a malleable metal coating (118) on the tapered portion of the distal tip. The malleable metal may be selected from suitable radiopaque materials such as gold or other easily solderable materials such as silver, platinum, palladium, rhodium, and alloys of the above. The tip also includes a radiopaque coil (112) which is bounded on its proximal end by a solder joint (114) and is joined with the end of the guidewire at (110). The radiopaque coil (112) may be made of known suitable materials such as platinum, palladium, rhodium, silver, gold, and their alloys. Preferred is an alloy containing platinum and a small amount of tungsten. The proximal and distal ends of coil (112) may be secured to the core wire by soldering.

Figure 3:
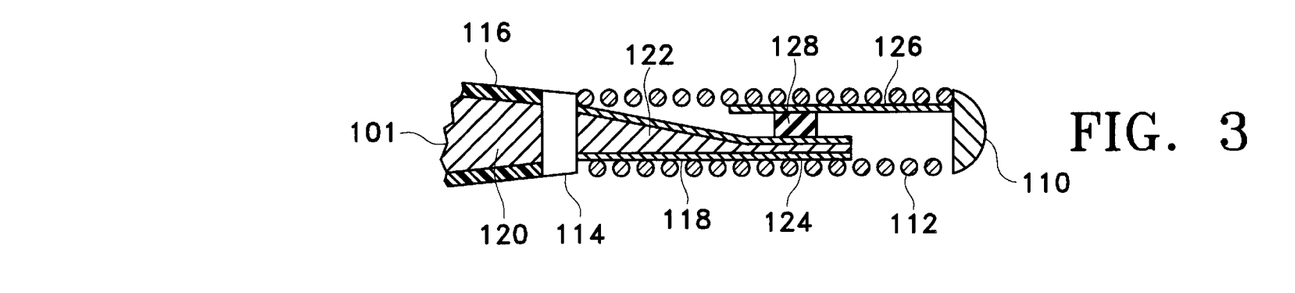
FIG. 3 is a partial cutaway side view of a second embodiment of the distal tip of the FIG. 1 device.

FIG. 3 shows a partial cutaway of another embodiment of the distal section (104) of FIG. 1. In this embodiment, the wire core (101) has a distal tapered section (122) with a solder joint (114) separating the two sections, and a constant diameter tip (124). The distal tip (124) may have constant diameter typically between about 0.002 and 0.005 inches, preferably about 0.003 inches. The distal tip (124) is preferably between about 1 and 5 cm in length, preferably about 2 cm but the portion of constant diameter extends for at least about 25% of the distance between the solderjoint (128) and the solderjoint (114). This constant diameter section marginally stiffens the distal tip assembly for enhanced control. The entire distal section (104) desirably is between about 20 and 50 cm, preferably about 25 cm in length. The maximum diameter of the proximal tapered portion (120) of the guidewire core typically is between about 0.005 and 0.020 inches, preferably about 0.010 inches. The distal tapered portion (122) and distal tip (124) are again shown with a malleable metal coating (118) such that the distal tapered portion (122) and distal tip (124) stay bent upon forming by the physician. In this embodiment, the fine wire coil (112) is bounded on its proximal end by a solder joint (114) and on its distal end by an end cap (110). The end cap (110) is connected to the guidewire by means of a metallic ribbon (126). The ribbon (126) may be made of stainless steel, platinum, palladium, rhodium, silver, gold, tungsten, and their alloys or other materials which are plastic and that are easily soldered. The ribbon (126) is soldered to the fine wire coil (112) and to the distal tip (124) of the distal section (104) of the guidewire at a solderjoint (128) such that the end cap (110) is secured against the fine wire coil (112).

Figure 4A:
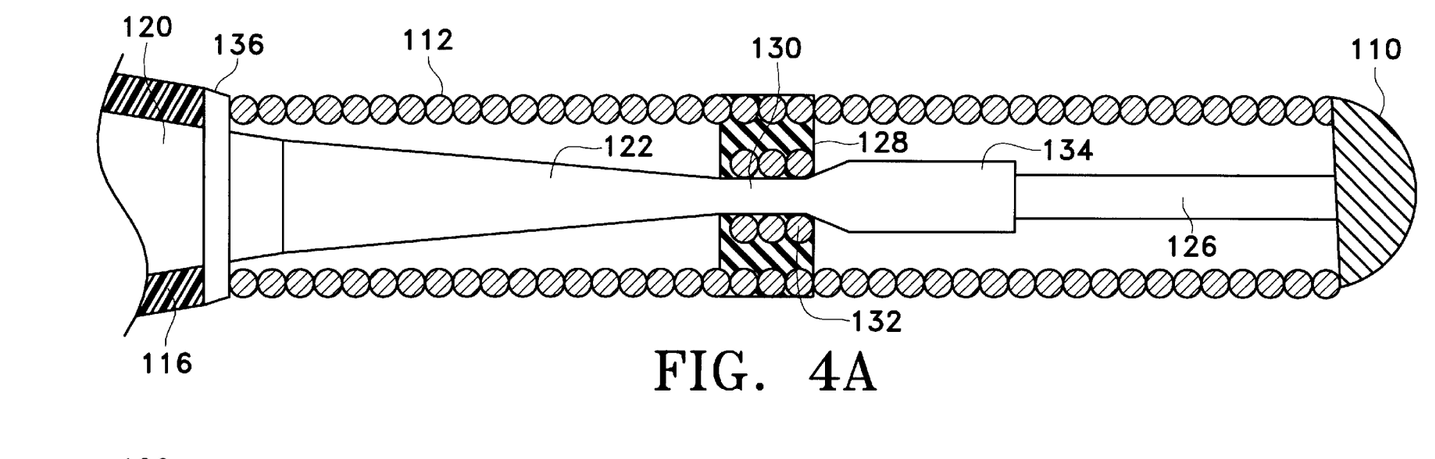
FIG. 4A is a partial cutaway side view of a third embodiment of the distal tip of the FIG. 1 device.
Figure 4B:
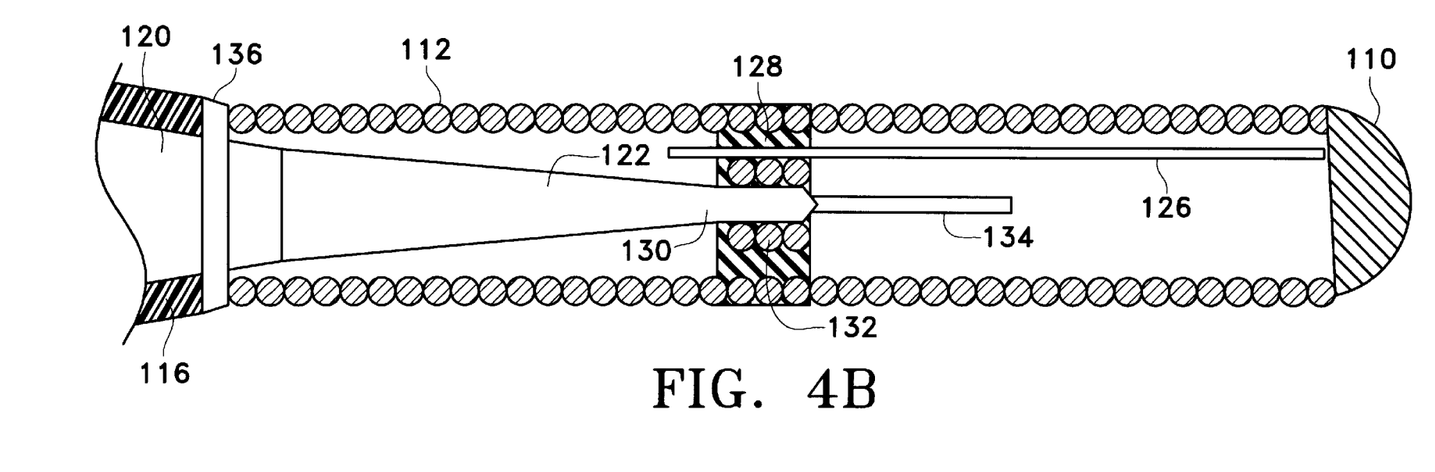
FIG. 4B is a partial cutaway top view of the embodiment shown in FIG. 4A.

FIGS. 4A and 4B show yet another embodiment of distal section (104) of FIG. 1. FIG. 4A shows a side view, partial cutaway of the guidewire distal section (104). The fine wire coil (112) may be bounded by a polymer adhesive (136) that joins the coil (112) to the core wire and an end cap (110) and further secured to the guidewire core by a solder joint (128). In this embodiment, the distal section (104) of the guidewire again comprises a tapered portion (120) that is proximal to the polymer adhesive (136) and a tapered portion (122) that is distal to the polymer adhesive (136). Tapered portion may be covered by the inventive polymeric tie layer (116) as described in detail below. The distal section (104) also comprises a smaller diameter portion (130) or "neck" that may be surrounded by optional inner coil (132). The inner coil (132) may be made of a suitable metallic material preferably that is easy to solder and preferably radiopaque. It is preferably platinum or stainless steel. One way to produce neck (130) is to flatten the distal portion of the guidewire (134) distal to the neck so that the resulting spade (134) is no longer of circular cross-section but rather is of rectangular shape. This may be more easily visualized in FIG. 4B since that Figure shows a cutaway top view of the guidewire shown in FIG. 4A. As in above-described embodiments, the end cap (110) is secured to the guidewire by a metallic ribbon (126). The solder joint (128) secures the guidewire core to the inner helical coil (132) which secures the end cap (110) via the ribbon (126) and further secures the outer fine wire coil (112). This configuration is especially valuable for use with guidewire materials which are not easily solderable. The solder joint need not adhere to the guidewire and yet the inner coil (132), ribbon (126), and outer fine wire coil (112) all are maintained as a single integral unit and have no chance of slipping proximally or distally on the guidewire assembly.

Although the embodiment described with reference to FIGS. 4A and 4B speaks generally of a guidewire made of a high elasticity alloy, materials for the guidewire and the ribbon such as stainless steel, platinum, palladium, rhodium and the like are suitable with that embodiment.

Figure 5:
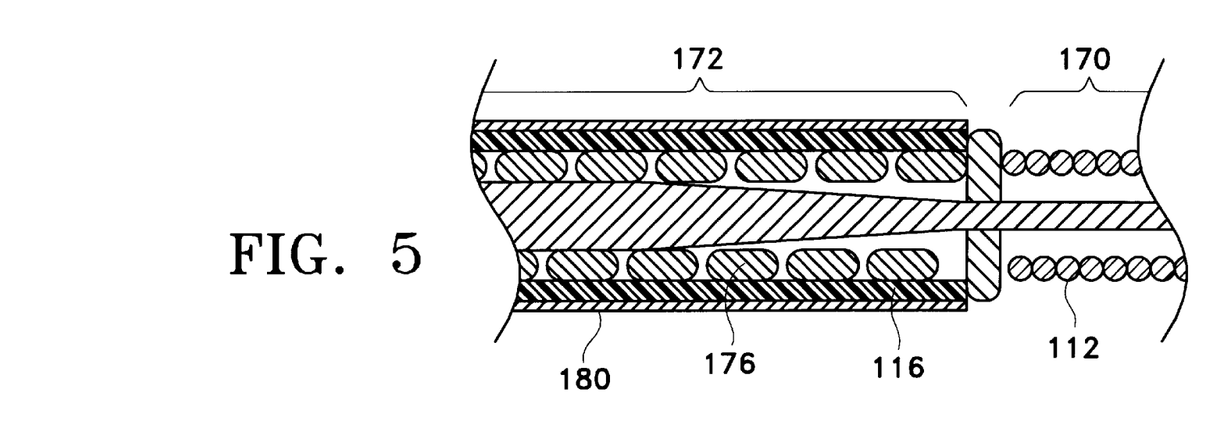
FIGS. 5 and 6 show midsection variations, in fragmentary cross-section, of the inventive guidewire.
Figure 6:
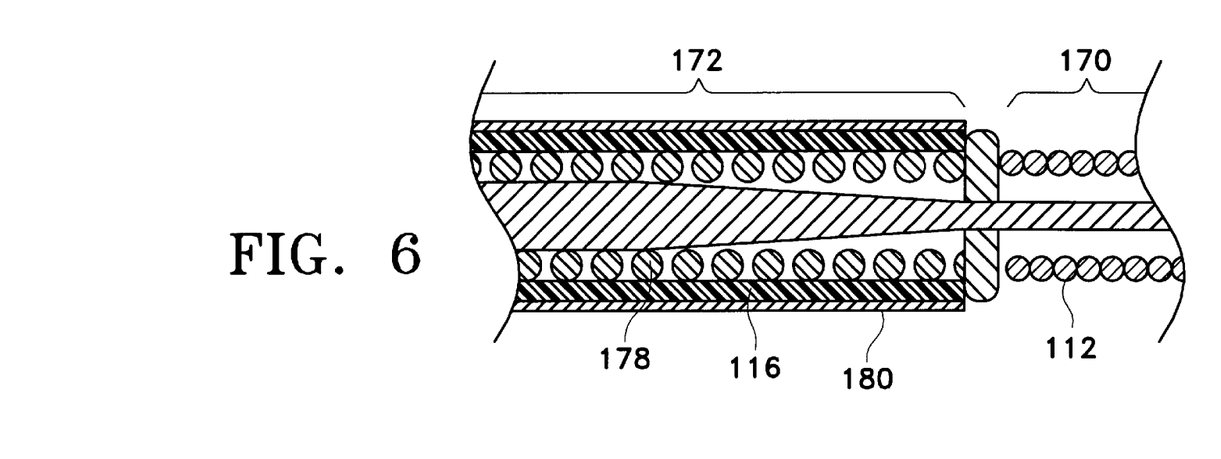

FIGS. 5 and 6 show partial fragmentary cross-sections of portions of the distal section (170) and the midsection (172) of a variation of the inventive guidewire assembly. In the variations shown in FIGS. 5 and 6, the core is ground to a smaller diameter to achieve a higher degree of flexibility in those regions. To provide additional column strength and torqueability, a flat wound ribbon (176) (in FIG. 5) or coil (178) (in FIG. 6) is disposed around the wire core (191). In addition, since many of the super-elastic alloys making up wire core (101) are not particularly radiopaque, it is often desirable to use radiopaque materials for the ribbon (176) or coil (178) so to permit the physician to observe the position of the guidewire assembly with greater ease. Indeed, it is not uncommon for the ribbons (176) or coils (178) to extend (in conjunction with the coils (112)) to 25–35 cm. from the distal tip of the catheter assembly. Again, it is not uncommon for the distal coil (112) to be itself up to about 10 cm. in length. Finally, it is desirable to use a smaller diameter wire in the more proximal coil (178) than the distal coil (112) to provide a radiopaque view and enhanced column strength to the guidewire belt with lower overall mass.

In addition, it is desirable to coat all or part of the guidewire with a lubricious coating material for improved frictional performance. When the lubricious coating is a hydrophilic polymer coating material, it is often desirable to use a tie layer (116) on the wire core (101). This is so because the hydrophilic coatings used in the art do not always bond satisfactorily to the materials used to construct the wire core. The tie layer then is chosen so that it may act as an intermediary bonding substrate for the wire core and the lubricious coating. In FIGS. 5 and 6, the tie layer (116) is shown as being placed over the midsection stiffeners (176) and (178). The tie layer (116) is preferably at least partially coated with hydrophilic polymer coating (180).

Suitable hydrophilic polymers include those made from monomers such as ethylene oxide and its higher homologs; 2-vinyl pyridine; N-vinylpyrrolidone; polyethylene glycol acrylates such as mono-alkoxy polyethylene glycol mono (meth) acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin; maleic anhydride; aldehydes. These monomers may be formed into homopolymers or block or random copolymers. The use of oligomers of these monomers in coating the guidewire for further polymerization is also an alternative. Preferred precursors include ethylene oxide; 2-vinyl pyridine; N-vinylpyrrolidone and acrylic acid and its salts; acrylamide and acrylonitrile polymerized (with or without substantial crosslinking) into homopolymers, or into random or block copolymers.

Additionally, hydrophobic monomers may be included in the coating polymeric material in an amount up to about 30% by weight of the resulting copolymer so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate. Preferred are ethylene, propylene, styrene, and styrene derivatives.

The lubricious polymeric coating may be cross-linked using various techniques, e.g., by light such as ultraviolet light, heat, or ionizing radiation, or by peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the monomers and polymers discussed above.

Polymers or oligomers applied using the procedure described below are activated or functionalized with photoactive or radiation-active groups to permit reaction of the polymers or oligomers with the underlying polymeric surface.

Suitable activation groups include benzophenone, thioxanthone, and the like; acetophenone and its derivatives specified as:

where
R$^1$ is H, R$^2$ is OH, R$^3$ is Ph; or
R$^1$ is H, R$^2$ is an alkoxy group including —OCH$_3$, —OC$_2$H$_3$, R$^3$ is Ph; or
R$^1$=R$^2$=an alkoxy group, R$^3$ is Ph; or
R$^2$=R$^2$=an alkoxy group, R$^3$ is H; or
R$^1$=R$^2$=Cl, R$^3$ is H or Cl.
Other known activators are suitable.

The polymeric coating may then be linked with the substrate using known and appropriate techniques selected on the basis of the chosen activators, e.g., by ultraviolet light, heat, or ionizing radiation. Crosslinking with the listed polymers or oligomers may be accomplished by use of peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the polymers and oligomers discussed above is also appropriate for this invention.

The polymeric coating may be applied to the guidewire by any of a variety of methods, e.g., by spraying a solution or suspension of the polymers or of oligomers of the monomers onto the guidewire core or by dipping it into the solution or suspension. Initiators may be included in the solution or applied in a separate step. The guidewire may be sequentially or simultaneously dried to remove solvent after application of the polymer or oligomer to the guidewire and crosslinked.

The solution or suspension should be very dilute since only a very thin layer of polymer is to be applied. We have found that an amount of oligomer or polymer in a solvent of between 0.25% and 5.0% (wt), preferred is 0.5 to 2.0% (wt), is excellent for thin and complete coverage of the resulting polymer. Preferred solvents for this procedure when using the preferred polymers and procedure are water, low molecular weight alcohols, and ethers, especially methanol, propanol, isopropanol, ethanol, and their mixtures. Other water miscible solvents, e.g., tetrahydrofuran, methylene dichloride, methylethylketone, dimethylacetate, ethyl acetate, etc., are suitable for the listed polymers and must be chosen according to the characteristics of the polymer; they should be polar because of the hydrophilic nature of the polymers and oligomers but, because of the reactivity of the terminal groups of those materials, known quenching effects caused by oxygen, hydroxyl groups and the like must be recognized by the user of this process when choosing polymers and solvent systems.

The lubricious hydrophilic coating is preferably produced using generally simultaneous solvent removal and crosslinking operations. The coating is applied at a rate allowing "sheeting" of the solution, e.g., formation of a visibly smooth layer without "runs". In a dipping operation for use with most polymeric substrates including those noted below, the optimum coating rates are found at a linear removal rate between 0.25 and 2.0 inches/sec, preferably 0.5 and 1.0 inches/sec.

The solvent evaporation operations may be conducted using a heating chamber suitable for maintaining the surface at a temperature between 25° C. and the glass transition temperature ($T_g$) of the underlying substrate. Preferred temperatures are 50° C. to 125° C. Most preferred for the noted and preferred solvent systems is the range of 75° to 110° C.

Ultraviolet light sources may be used to crosslink the polymer precursors onto the substrate. Movement through an irradiation chamber having an ultraviolet light source at 90–375nm (preferably 300–350nm) having an irradiation density of 50–300 mW/cm$^2$ (preferably 150–250 mW/cm$^2$) for a period of three to seven seconds is desired. Passage of a guidewire core through the chamber at a rate of 0.25 to 2.0 inches/second (0.5 to 1.0 inches/second) in a chamber having three to nine inches length is suitable. When using ionizing radiation, a radiation density of 1 to 100 kRads/cm$^2$ (preferably 20 to 50 kRads/cm$^2$) may be applied to the solution or suspension on the polymeric substrate.

Exceptional durability of the resulting coating is produced by repetition of the dipping/solvent removal/irradiation steps up to five times. Preferred are two to four repetitions.

As mentioned above, we have found that it is often desirable to incorporate a "tie" layer as a coating between the outer lubricious polymeric surface and the wire core to enhance the overall adhesion of the outer lubricious polymeric surface to the core. Of course, these materials must be able to tolerate the various other solvents, cleaners, sterilization procedures, etc. to which the guidewire and its components are placed during other production steps.

Choice of materials for such tie layers is determined through their functionality. Specifically, the materials are chosen for their affinity or tenacity to the outer polymeric lubricious or hydrophilic coating. Clearly, the tie layer material must be flexible and strong. The tie layers may be placed onto the guidewire core in a variety of ways. The polymeric material may be extrudable and made into shrinkable tubing for mounting onto the guidewire through heating. It may be placed onto the guidewire core by dipping, spraying, shrink wrapping of polymeric tubing or other procedure. One quite desirable procedure involves the placement of a polymeric tubing of a fusible polymer, e.g., polyurethane, on the guidewire core which, in turn, is covered with a heat shrink tubing such as polyethylene. The outer tubing is shrunk down and the inner tubing is fused onto the guidewire core to form a tie layer. The thickness of the tie layer may be from 0.0003" to about 0.015". The tie layer is preferably 0.0004" to 0.003" in thickness. The melt temperature of the tie layer polymer desirably is appropriately chosen to fuse at the heat shrink temperature of the outer tubing. The outer shrink tubing is then simply peeled off, leaving the tie layer exposed for treatment with the lubricious coating.

We have found that various NYLON's, polyethylene, polystyrene, polyurethane, and polyethylene terephthalate (PET) make excellent tie layers. Preferred are polyurethane (Shore 50A–80D) and PET. Most preferred is polyurethane. These materials may be formulated or blended to include radio opaque materials such as barium sulfate, bismuth trioxide, bismuth carbonate, tungsten, tantalum or the like.

As noted above, another manner of applying a tie layer is by heat-shrinking the tubing onto the guidewire. The guidewire core is simply inserted into a tubing of suitable size—often with a small amount of a "caulking" at either end to seal the tubing from incursion of fluids or unsterile materials from beneath the tubing. The tubing is cut to length and heated until it is sufficiently small in size. The resulting tubing tie layer desirably is between about 0.0003 and 0.015 inches in thickness. The thinner layers are typically produced from polyurethane or PET. The layer of lubricious polymer is then placed on the outer surface of the shrunk tubing.

To this point, tie layer (116) has been shown and discussed as a generally single layer polymeric material, the primary purpose of which is to provide an intermediary bonding substrate as described above between the core wire and the lubricious coating. In addition, however, the structure of the tie layer may advantageously enhance the functional performance of the guidewire in other ways. That is for a given wire core construction the tie layer may be constructed in such a manner as to change the flexibility, torsional rigidity, or column strength of specific sections of a guidewire over that of the wire core without such a tie layer. For instance, it may be desirable to use a number of sections of polyurethane having differing hardnesses or cross-sectional properties.

Figure 7:
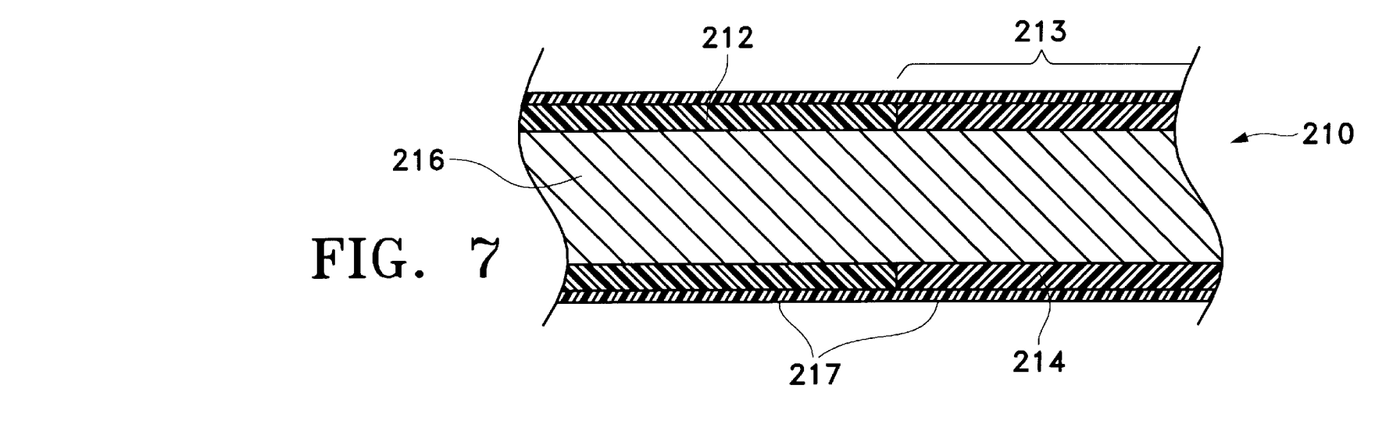
FIG. 7 shows a cross-section of a fragment of a guidewire constructed according to one embodiment of the present invention.

FIG. 7 shows a section of a guidewire (210) generally of the type shown in FIG. 1, designed for use with a catheter or the like for accessing an internal target site within a body, typically along a tortuous vessel path.

Wire core (216) has a sectioned polymeric tie layer (213) coaxially located about a length of the wire core. The polymeric tie layer (213) comprises at least two axially spaced sections (212) and (214) as shown in FIG. 7. A substantial portion of each of the adjacent sections (212) and (214) of polymeric tie layer (213) is covered by a lubricious coating (217) of the type described above. While FIG. 7 shows only two adjacent sections, it should be recognized that many sections may be employed along the length of the wire core (216). Preferably each of the polymeric sections that may be employed along the length of wire core (216) is covered or coated with the lubricious coating (217).

The sectioned tie layer according to the present invention is constructed to provide two important functions. First, as is common with tie layers in general, the polymeric tie layer (213) is selected to provide an intermediary bonding substrate as described in detail above. Second, the multiple tie layer sections (212 and 214) may be adapted to alter the flexural stiffness, torsional stiffness, and/or column stiffness of the wire core to advantageously tailor the functional properties of a given wire core along its elongated length. For instance, section 212 may be of a first material, being of a different flexibility than section 214 constructed of a second material.

In this way a wire core may be provided with increased performance in certain applications. For example, along sections of guidewire (100) of FIG. 1 that require a hydrophillic coating for reduced friction, it may also be desirable to have to tie layer (116) increase or decrease in flexibility towards the distal end (104).

In a preferred embodiment, the multiple sections (212 and 214) of tie layer (213) are made from a common material wherein one of the material's characteristic properties (hardness, for instance) is varied to obtain the advantages just mentioned. Most preferably the tie layer sections are constructed of polyurethane having different hardnesses, or durometer, in the range of about Shore 50A–80D.

In a most preferred embodiment, at least one tie layer section (214) increases in hardness (and consequently decreases in flexibility) from a tie layer section located proximally adjacent (212). Of course, the greatest effect on the wire core's functional properties are obtained when adjacent tie layer sections have hardnesses that are substantially different.

Additionally it may be highly desirable to have at least one proximally located tie layer section of lowest flexibility, at least one middle tie layer section of highest flexibility, and at least one distal tie layer section of a flexibility lower than the middle tie layer sections. The increased diameter provided by the tie layer maintains column strength throughout, while allowing a sufficiently stiff proximal section to facilitate guidewire advancement, a middle section of increased flexibility to facilitate maneuvering through tortuous vasculature, and a somewhat stiffer distal section for enhanced steerability and branch selectability. Such a configuration is illustrated in FIG. 8.

Figure 8:
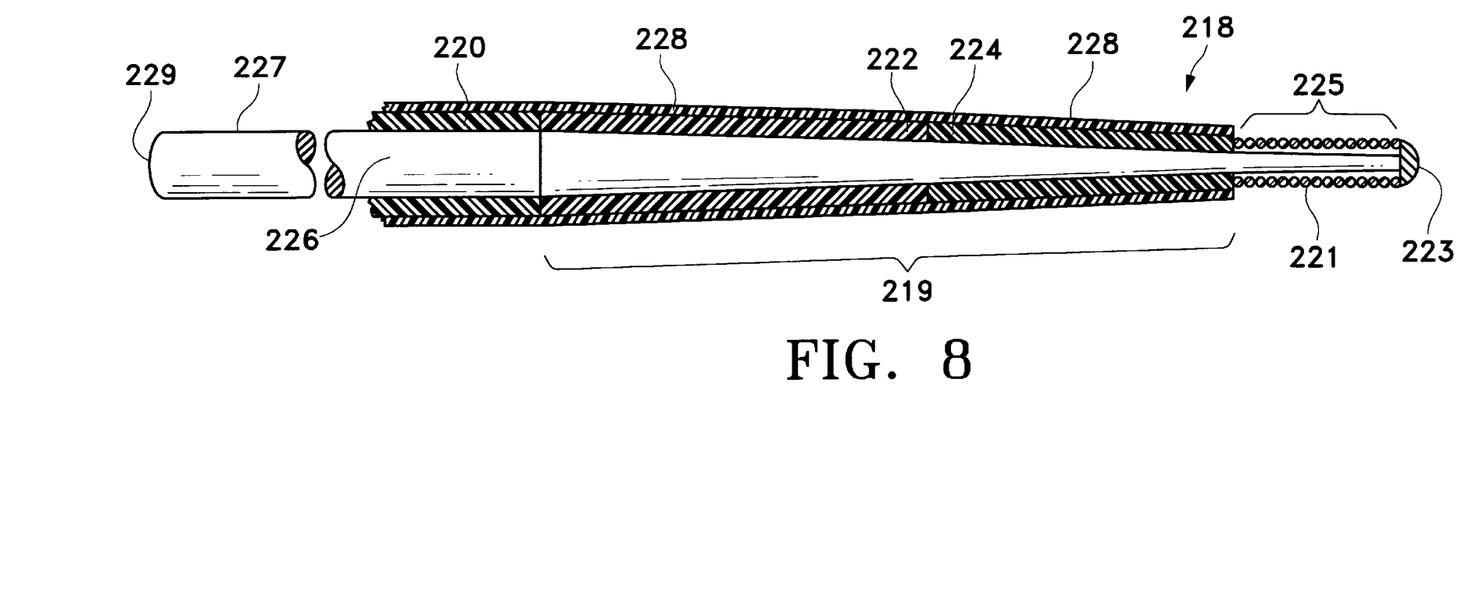
FIG. 8 shows a fragmentary cross-section of a guidewire having an distal section constructed according to the embodiment of the present invention as shown in FIG. 7.

FIG. 8 shows a guidewire section (218) constructed with a sectioned tie layer. Guidewire section (218) has a distal portion (219), a distal tip portion (225) and a proximal end (229). Guidewire section (218) has an elongated wire core (226), which may taper as shown, and a distal section having a fine wire coil (221) and endcap (223) of the construction as previously discussed. Guidewire section (218) further includes a sectioned tie layer having a proximal tie layer section (220), a middle tie layer section (222), and a distal tie layer section (224). Each of the tie layer sections preferably has a different flexibility from axially adjacent tie layer sections. The tie layer sections are preferably made of polyurethane having hardnesses that differ from adjacent tie layer sections. In a preferred embodiment, proximal tie layer section (220) has the highest hardness, middle tie layer section (222) has a lower hardness, and distal tie layer section (224) has a greater hardness than middle tie layer section (222). As an example, proximal section (220) may have a hardness in the range of about 40D–85D, middle tie layer section (222) may have a hardness in the range of about 50A–90A and distal tie layer section (224) may have a hardness in the range of about 75A–60D. Preferably proximal section (220) may have a hardness in the range of about 40D–75D, middle tie layer section (202) may have a hardness in the range of about 55A to 75A, and distal the layer section (224) may have a harness in the range of about 95A to 55D.

Figure 9:
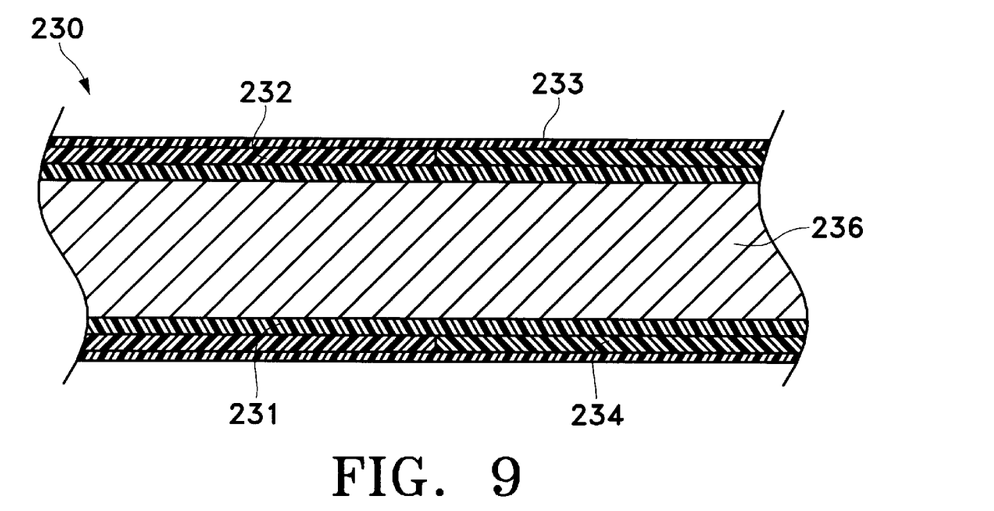
FIGS. 9 and 10 are cross-sectional views of alternate guidewire constructions according to another embodiment of the present invention.

FIG. 9 shows another embodiment of the inventive guidewire section, this one being a composite guidewire section (230) which has an elongated wire core (236) and a tie layer of multiple radial layers, at least one of which is axially sectioned as previously described. Disposed generally coaxially around wire core (236) is a first inner tie layer (231). Around first inner tie layer (231) is a sectioned tie layer having a proximal section (232) and a distal tie layer section (234). The sectioned tie layer is coated at least partially with a lubricious coating (233). Each of the sections may be of a different tie layer material or preferably of a common material with a varying material property, such as hardness. Again, the tie layer section materials are preferably made from polyurethane or PET of different hardnesses. In a preferred embodiment, distal tie layer section (234) would have the highest hardness (and consequently the least flexibility), and tie layer sections (232) and (231) would be constructed of polyurethane having a lower hardness value.

Figure 10:
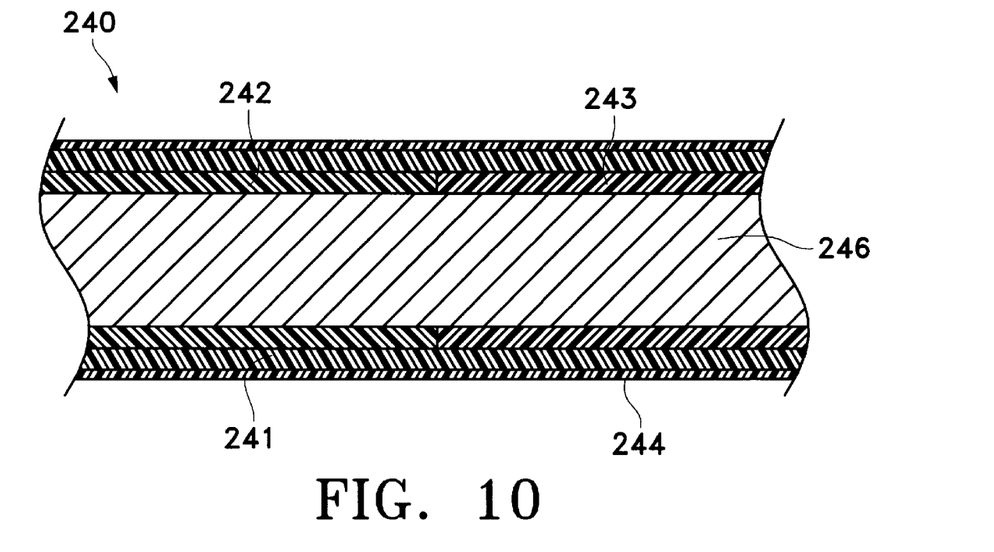

FIG. 10 shows another embodiment of a composite guidewire section (240) that is very similar to that of FIG. 9 except that the sectioned tie layer having at least proximal section (242) and distal section (243) is closest to the wire core (246) and is at least partially covered by an outer tie layer section (241). Outer tie layer (241) is at least partially covered with a lubricious coating (244).

The sectioned tie layer described in FIGS. 9 and 10 may have many axially spaced sections or may have additional radial layers. Inner tie layer (231) of FIG. 9 and outer tie layer (241) of FIG. 10 may each comprise several sections as well. The radial layers and longitudinal sections can be made using any of the techniques discussed above. For example each radial layer or longitudinal section may be put in place and shrunk onto the guidewire using heat or all the sections may be placed over the wire core (and each other) and heat shrunk simultaneously. Preferably the various layers and sections of fusible polyurethane are put in place and a heat shrinkable polymeric tube is place over the entire assembly. As previously discussed, the outer tubing is heat shrunk down and the various layers and sections are fused to the wire core and each other. The outer polymeric tube is then peeled off and the lubricious coating is applied.

Figure 11:
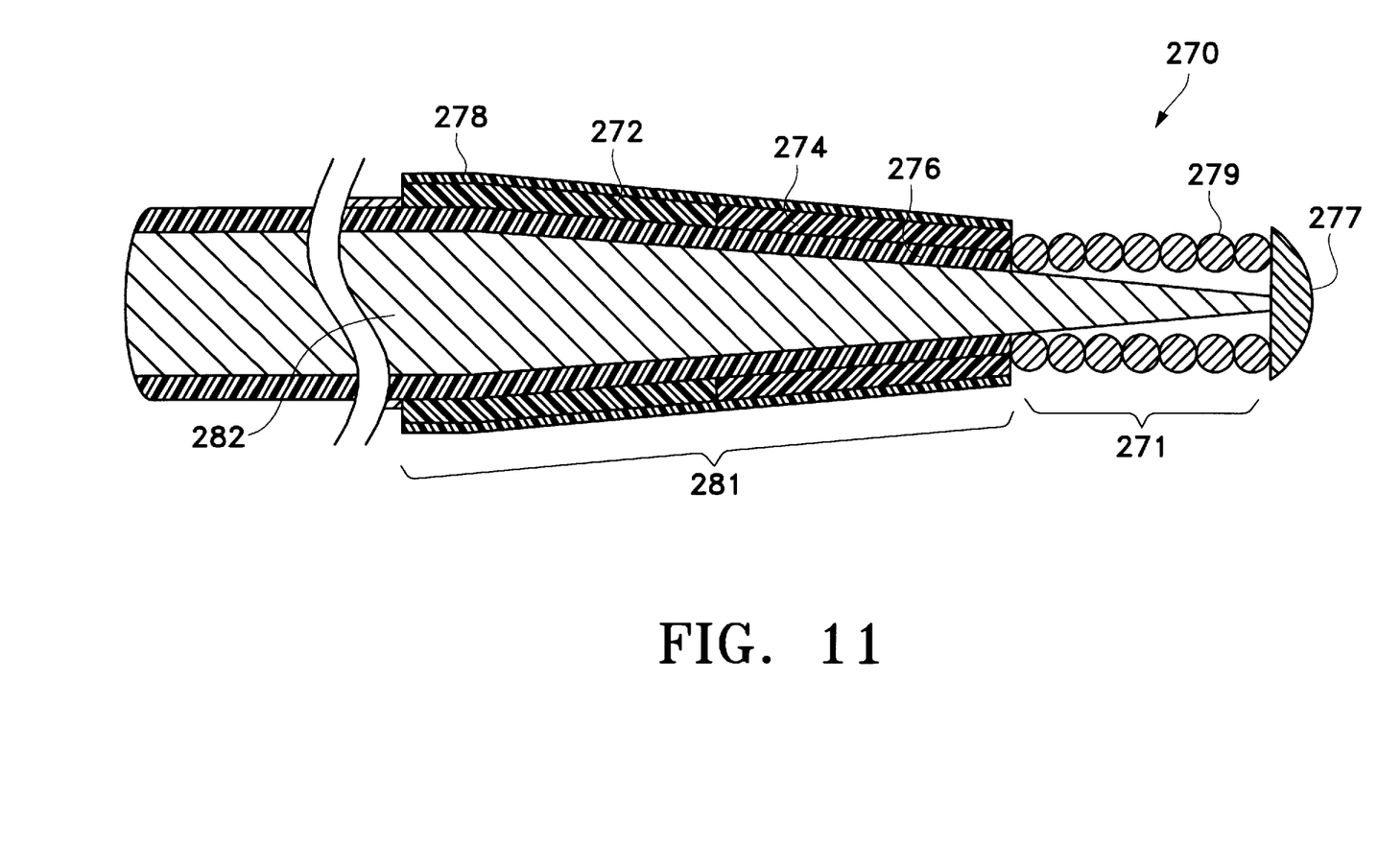
FIGS. 11 is a fragmentary cross-sectional view of a guidewire having an distal section constructed according to the embodiment of the present invention as shown in FIGS. 9 and 10.

The general inventive composite guidewire section of FIGS. 9 or 10 may be located at a distal tip of a guidewire as shown, for example, in FIG. 11. FIG. 11 shows a distal section of guidewire (270) having wire core (282), a distal tip portion (271), and a distal portion (281) comprising a fine wire coil (279) and endcap (277). The distal tip portion (271) may be constructed according to any of the distal tip embodiments described above with regards to FIGS. 2–6. Wire core (282) has a composite tie layer disposed about it in a generally coaxial relationship. The composite tie layer comprises a first inner tie layer (276) and an outer sectioned tie layer having a proximal tie layer (272) and a distal tie layer (274). The outer sectioned tie layer is coated with a lubricious coating (278). The varying materials and hardnesses may be the same as described above for FIG. 10.

Figure 12:
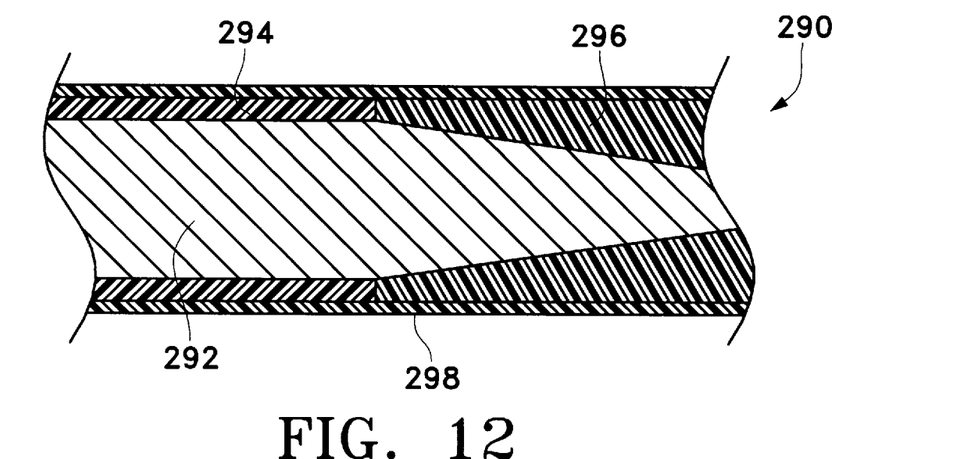
FIG. 12 is a cross-sectional view illustrating another embodiment of a guidewire section having variable thickness polymeric layers.

FIG. 12 shows yet another inventive embodiment of a guidewire section (290) having a sectioned tie layer involving at least one section having a varying cross-section. Guidewire section (290) is shown having wire core (292) and a sectioned tie layer having at least a proximal tie layer section (294) and a axially adjacent distal tie layer section (296). Distal tie layer section (296) has a varying cross-section as the thickness increases distally. Further, when the wire core (292) has a taper section, as shown, the thickness of distal tie layer section (296) may be increased correspondingly to provide a relatively constant diameter. The two tie layer sections (294) and (296) may be of different material or of a common material having different hardnesses, as has been described above. Preferably, the tie layer sections are constructed of polyurethane of different hardnesses, distal tie layer section (296) having a greater hardness. Constructed in this manner of distal tie layer section (296) having a higher hardness and an increasing thickness distally, even greater opportunity exists to increase the stiffness of the guidewire distally as desired. Additionally, the tapered tie layer section provides of a smooth gradient of changing flexibility.

Figure 13:
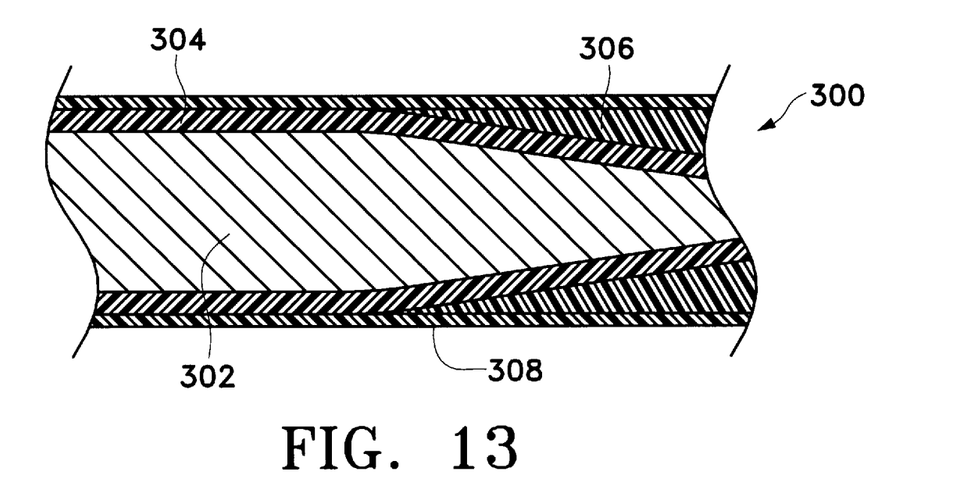
FIGS. 13 is a cross-sectional view illustrating an alternate construction of another embodiment of a guidewire section having polymeric tie layers, at least one of which being tapered and which the polymeric layers at least partially overlap each other.

FIG. 13 shows another embodiment of a guidewire involving a sectioned, composite tie layer involving at least one layer having a varying cross-section. FIG. 13 shows guidewire section (300) having core wire (302) and a sectioned, composite tie layer comprising a first inner tie layer (304) and a second outer tie layer (306) having a varying thickness. At least a portion of first inner layer (304) overlaps second outer tie layer (306). Although the desired flexural and torsional stiffness of the tie layer may depend upon the application and location on the guidewire, outer layer (306) is preferably constructed to be less flexible than that of immediately adjacent and overlapping tie layer section (304).

The inventive guidewires as described above allow the flexural and torsional characteristics to be profiled according to the requirements of a given procedure or desire of the physician operator. Although preferred embodiments of the present invention have been described, it should be understood that various changes, adaptations, and modifications may be made therein without departing from the spirit of the invention and the scope of the claims which follow.

We claim:

1. A guidewire section for use with a catheter comprising an elongated, flexible wire core having a polymeric tie layer coaxially located about a length of the wire core surface, said tie layer having at least two axially spaced tie layer sections, each of said tie layer sections being of a different flexibility than a axially adjacent tie layer section, and at least a portion of said polymeric tie layer having an exterior coating of lubricious material.

2. The guidewire section according to claim 1 wherein each of said tie layer sections are individually selected from the group consisting of NYLON, polyethylene, polystyrene, polyurethane, and polyethylene terephthalate.

3. The guidewire section according to claim 2 wherein at least two tie layer sections are comprised of polyurethane, the polyurethane of each of said tie layer sections having a hardness different than that of axially adjacent tie layer sections.

4. The guidewire section according to claim 3 wherein the wire core has a proximal end and a distal end and the hardness of said tie layer sections progressively increases from the tie layer section located most proximally through each of the axially adjacent tie layer sections.

5. A guidewire section for use with a catheter comprising an elongated, flexible wire core having a polymeric tie layer coaxially located about a length of the wire core surface, said tie layer having at least:
   (a) a proximal tie layer section having the lowest flexibility;
   (b) a middle tie layer section having the highest flexibility;
   (c) a distal tie layer section having a flexibility lower than that of said middle tie layer; and at least a portion of said polymeric tie layer having an exterior coating of lubricious material.

6. The guidewire section according to claim 5, wherein said tie layer sections are made from polyurethane having different hardnesses.

7. The guidewire section according to claim 6 wherein said proximal tie layer section has a hardness in the range of about 40D–75D, said middle tie layer section has a hardness in the range of about 55A to 75A, and said distal tie layer section has a hardness in the range of about 95A to 55D.

8. A guidewire for use with a catheter or the like comprising an elongated, flexible metal wire core having a flexible, torqueable proximal section, a more flexible intermediate section, and a most flexible distal section, said distal section having a polymeric tie layer having a proximal tie layer section and at least one distal tie layer section, each of said sections being more or less flexible than adjacent sections, and at least a portion of said tie layer having an exterior coating of lubricious material;
   wherein said proximal tie layer section and said distal tie layer section or sections are comprised of polyurethane, the polyurethane of each of said tie layer sections having a hardness different than that of adjacent tie layer sections.

9. The guidewire according to claim 8 wherein the hardness of said tie layer sections progressively increases from the proximal tie layer section through each of the distal tie layer sections.

10. The guidewire according to claim 8 wherein said distal wire core section is tapered.

11. A guidewire section for use with a catheter or the like comprising an elongated, flexible metal wire core having a composite polymeric tie layer coaxially located about a length of the wire core, said polymeric tie layer having a substantially continuous first layer and a second layer having at least two sections, each of said second layer sections being more or less flexible than adjacent second layer sections.

12. The guidewire section of claim 11 wherein said continuous first layer encases and contacts said wire core and said second layer sections are disposed over said continuous first layer.

13. The guidewire section of claim 11 wherein each of said second layer sections encases and contacts said wire core and said continuous first layer is disposed over said second layer sections.

14. The guidewire section of claim 12 wherein said each of said second layer sections has greater of lesser flexibility than adjacent second layer sections.

15. The guidewire section of claim 13 wherein said each of said second layer sections has greater of lesser flexibility than adjacent second layer sections.

16. The guidewire section according to claim 12 wherein each of said first and second layers are comprised of at least one of NYLON, polyethylene, polystyrene, polyurethane, and polyethylene terephthalate.

17. The guidewire section according to claim 13 wherein each of said first and second layers are comprised of at least one of NYLON, polyethylene, polystyrene, polyurethane, and polyethylene terephthalate.

18. The guidewire section according to claim 12 wherein each of said second layer sections and continuous first layer section are comprised of polyurethane, the polyurethane of each of said second layer sections having a hardness different than that of axially adjacent second layer sections.

19. The guidewire section according to claim 13 wherein each of said second layer sections and continuous first layer section are comprised of polyurethane, the polyurethane of each of said second layer sections having a hardness different than that of axially adjacent second layer sections.

20. The guidewire section according to claim 12 wherein the hardness of said continuous first layer is substantially less than that of each of the second layer sections.

21. The guidewire section according to claim 20 wherein said first continuous layer has a hardness in the range of about 55A–75A and said second layer sections have a hardness in the range of about 95A to 60D.

22. A guidewire section for use with a catheter comprising an elongated, flexible wire core having a polymeric tie layer coaxially located about a length of the wire core surface, said tie layer having at least two axially spaced tie layer sections, one of said tie layer sections having a variable thickness along its length, and at least a portion of said polymeric tie layer having an exterior coating of lubricious material.

23. The guidewire section according to claim 22 wherein said tie layer comprises a first tie layer section and a second tie layer section, said second tie layer section having a varying thickness and said first and second tie layer sections axially overlap at least over a portion of their length.

* * * * *

UNITED STATES PATENT AND TRADEMARK OFFICE

CERTIFICATE OF CORRECTION

PATENT NO. : 5,772,609

DATED : June 30, 1998

INVENTOR(S) : Nguyen et al.

It is certified that error appears in the above-identified patent and that said Letters Patent is hereby corrected as shown below:

*Column 8, line 19*: please change "$R^2 = R^{2''}$" to -- $R^1 = R^2$ --.

Signed and Sealed this

Sixth Day of October, 1998

Attest:

BRUCE LEHMAN

Attesting Officer    Commissioner of Patents and Trademarks